(12) United States Patent
Deprey et al.

(10) Patent No.: US 12,076,458 B2
(45) Date of Patent: Sep. 3, 2024

(54) DISINFECTION PROCESS SAMPLING DEVICE

(71) Applicant: American Sterilizer Company, Mentor, OH (US)

(72) Inventors: Eric Deprey, Minneapolis, MN (US); Martin J Kaib, Minneapolis, MN (US); Maruti Sinha, Minneapolis, MN (US); Adam Zutz, Minneapolis, MN (US); Judson A. Herrig, Minneapolis, MN (US)

(73) Assignee: American Sterilizer Company, Mentor, OH (US)

( * ) Notice: Subject to any disclaimer, the term of this patent is extended or adjusted under 35 U.S.C. 154(b) by 712 days.

(21) Appl. No.: 17/315,932

(22) Filed: May 10, 2021

(65) Prior Publication Data

US 2021/0353812 A1 Nov. 18, 2021

Related U.S. Application Data

(60) Provisional application No. 63/024,305, filed on May 13, 2020.

(51) Int. Cl.
*A61L 2/28* (2006.01)
*G01N 1/22* (2006.01)
*G01N 33/00* (2006.01)

(52) U.S. Cl.
CPC ............... *A61L 2/28* (2013.01); *G01N 1/2226* (2013.01); *G01N 1/2273* (2013.01); *G01N 33/0004* (2013.01); *A61L 2202/121* (2013.01); *A61L 2202/122* (2013.01); *A61L 2202/14* (2013.01)

(58) Field of Classification Search
CPC ............... B01N 1/2226; B01N 1/2273; B01N 33/0004; A61L 2/28; A61L 2202/121; A61L 2202/122; A61L 2202/14
See application file for complete search history.

(56) References Cited

U.S. PATENT DOCUMENTS

| 4,247,517 A * | 1/1981 | Sanderson | A61L 2/26 220/201 |
| 7,357,896 B2 * | 4/2008 | Morrison | A61L 2/208 435/31 |

FOREIGN PATENT DOCUMENTS

JP 5851054 B2 * 2/2016 ............... G01N 1/22

\* cited by examiner

*Primary Examiner* — Jennifer Wecker
*Assistant Examiner* — Brady C Pilsbury

(57) ABSTRACT

Various examples disclosed relate to a device for use in a disinfection process. The device can include, for example, a sampling assembly capable of a first position and a second position, wherein the sampling assembly is configured to be used inside a sterilization system. The sampling assembly can include a top portion, a bottom portion, at least one seal therebetween such that the top portion and the bottom portion form an airtight compartment when in the first position, a central pin running through the top portion and bottom portion, and an actuator configured to move the sampling assembly between the first position and the second position along the central pin during a portion of the disinfection process, such that the sampling assembly can collect a sample of atmosphere within the disinfection system.

13 Claims, 6 Drawing Sheets

DISINFECTION PROCESS SAMPLING DEVICE

PRIORITY CLAIM

This application claims priority and benefit of U.S. Provisional application with Ser. No. 63/024,305, filed May 13, 2020, entitled DISINFECTION PROCESS SAMPLING DEVICE, which is herein incorporated by reference in its entirety.

BACKGROUND

Sterilization and disinfection systems, for example those systems used to sterilize medical equipment and devices, often are validated prior to use. Validation can, for example, ensure that the sterilization or disinfection system is functioning properly and killing or disabling a sufficient amount of microorganisms to sterilize the equipment being treated. In some cases, validation can include confirming the amount or type of chemical composition inside a sterilization chamber or disinfection environment.

In a sterilization or disinfection device, cycles can generally contain a number of phases. For example, many sterilization or disinfection cycles can include a conditioning phase, such as where a vacuum is created in the system, an injection phase where a sterilant or disinfectant is inserted into the system, a sterilization or disinfection phase where the products are sterilized or disinfected by the sterilant or disinfectant, and a ventilation phase where the sterilant or disinfectant is vented out of the system. Due to these various phases, the amount of microorganisms and the amount of sterilant or disinfectant in the system can significantly vary over the course of the system cycle.

Conventionally, a resistometer can be used to verify sterilization or disinfection systems to expose biological or chemical indicators to the environment in the system and determine whether sufficient sterilization or disinfection is occurring during the cycle. Where a resistometer is used, the biological or chemical indicators remain exposed to the atmosphere in the sterilization system throughout the duration of the sterilization or disinfection cycle, through all phases of the cycle. For this reason, verification of a sterilization or disinfection system with a resistometer cannot indicate at what point in the cycle sterilization or disinfection can occur, to what degree, or map sterilization or disinfection to various phases of the system cycle.

SUMMARY OF THE DISCLOSURE

Disclosed herein is an apparatus and associated methods for analyzing the environment of a sterilizing or disinfecting instrument, such as detecting the number of microorganisms present with a biological indicator, or detecting the type or make-up of sterilant, disinfectant, or other chemicals present in the sterilizing or disinfecting instrument. The sampling apparatus can alternatively be used for measuring temperature, pressure, humidity, or other parameters during a sterilization or disinfection process. The sampling apparatus can provide a controlled environment to minimize the effect of other possible dynamic effects for better understanding of the sterilization or disinfection process.

Verification of sterilization or disinfection systems or environments can allow users to ensure that the products they are sterilizing, or disinfecting are, in fact, sterile or disinfected after running the products through a system cycle. Verification can, for example, be performed with external sterilization or disinfection verification tools, such as a resistometer that runs in parallel with a sterilization system while cycling. In this case, the resistometers is hooked up to the same sterilant/disinfectant, gas, vacuum, or other incoming sources as the system, and a sterilization or disinfection cycle is run on the system. The atmosphere in the resistometer theoretically reflects the atmosphere inside the system or environment.

Often, biological or chemical indicators are inserted into the resistometer. Biological indicators can be used in such an analysis. In general, biological indicators can be measured for a D-value indicating how long it takes to reduce a microorganism population by 90%, or the time needed to 1-log reduction of microorganisms. Chemical indicators, by contrast, can indicate whether an amount of a particular chemical, such as a component of a sterilant, is present. Both biological and chemical indicators can be expensive.

In a resistometer validation method, the indicators can be exposed to the external atmosphere throughout the duration of the sterilization or disinfection cycle. The user can then remove the indicators from the resistometer after the cycle is complete, and determine whether the atmosphere in the resistometer validates the sterilizing or disinfecting system.

The system and methods disclosed herein are directed to a sampling assembly for verification of a sterilization or disinfection process and system that allows for temporal sampling throughout the cycle. For example, the sampling assembly can be opened to expose biological or chemical indicators to the atmosphere in the sterilization chamber or disinfection environment, and subsequently closed while the sterilization or disinfection cycle is still running.

Additionally, the sampling assembly can reside in the sterilization or disinfection chamber itself of the sterilization or disinfection system. For this reason, the sampling assembly does not collect samples in parallel, and instead can sample the atmosphere inside the sterilization or disinfection system.

In an example, a device for use in a sterilization or disinfection process can include a sampling assembly capable of a first position and a second position, wherein the sampling assembly is configured to be used inside a sterilization or disinfection system. The sampling assembly can include a top portion, a bottom portion, at least one seal therebetween such that the top portion and the bottom portion form an airtight compartment when in the first position, a central pin running through the top portion and bottom portion, and an actuator configured to move the sampling assembly between the first position and the second position along the central pin during a portion of the sterilization or disinfection process, such that the sampling assembly can collect a sample of atmosphere within the sterilization or disinfection system.

In an example, a method of validating a sterilizing or disinfecting system can include situating a sampling assembly in a chamber of the sterilizing or disinfecting system, the sampling assembly comprising a top portion, a bottom portion, and at least one seal therebetween such that the top portion and the bottom portion form an airtight compartment; running a sterilization or disinfection cycle on the sterilizing or disinfecting system; opening the sampling assembly during a portion of the sterilization or disinfection cycle; collecting a sample in the sampling assembly; and analyzing the sample.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure describes, among other things, devices and methods for validating a sterilization or disinfection system by internally testing the sterilization or disinfection system. As used herein, "disinfection," "disinfecting," and "disinfectant" can include methods, devices, and compositions for reduction of microorganisms in an environment, such as by the process of cleaning something to destroy or disable those microorganisms, which may include harmful pathogens in their vegetative state and reducing their amount to a non-threatening level. As used herein, "sterilization," "sterilizing," and "sterilant" can include methods, devices, and compositions for killing or inactivating substantially all microorganisms from a product or surface either in a vegetative or spore state. Sterilization can include, for example, a 12-log reduction of microorganisms. Disinfection can include sterilization.

Figure 1:
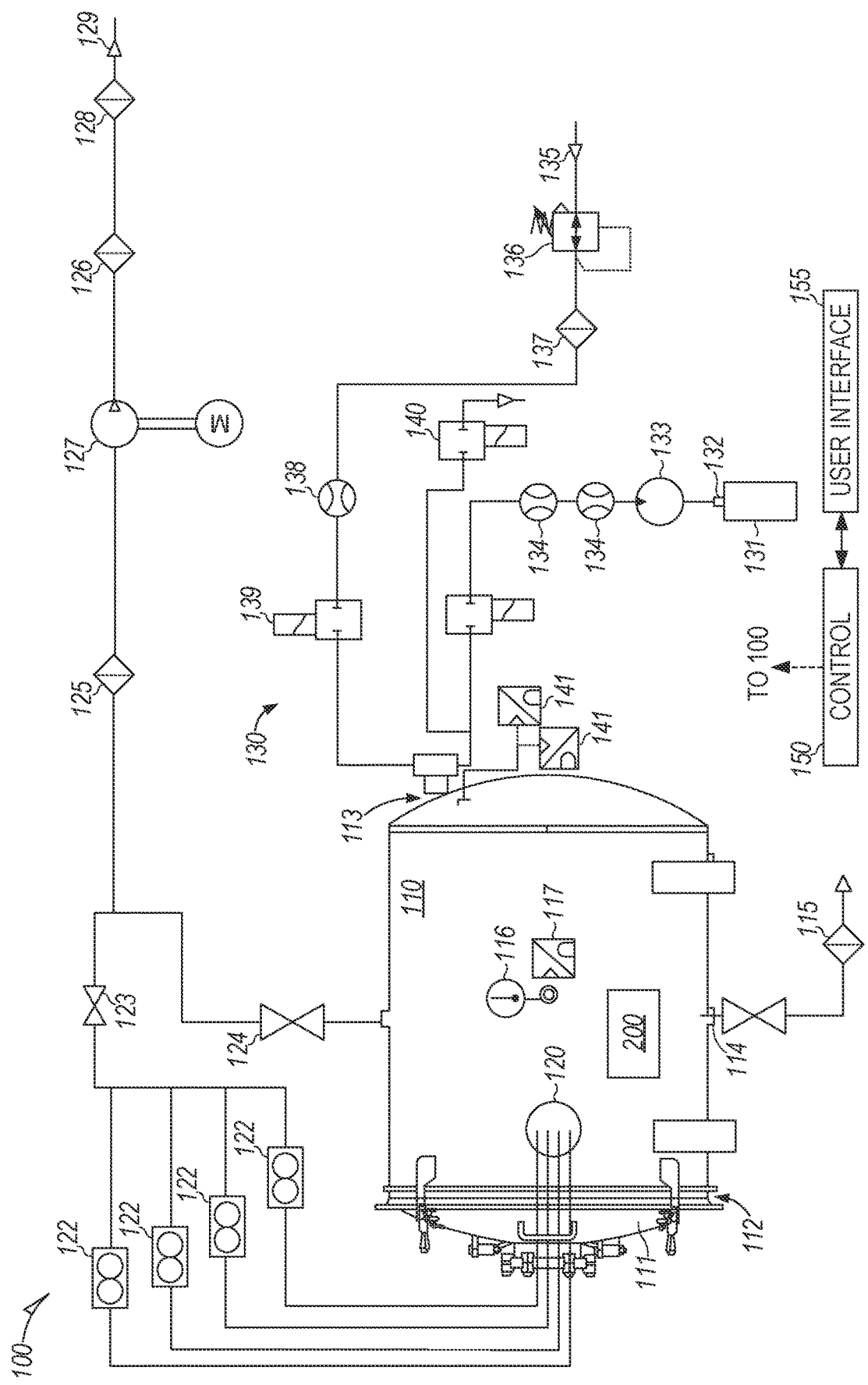
FIG. 1 is a schematic diagram of an example sterilization system.

FIG. 1 is a schematic diagram of an example sterilizing system 100 in which a sampling assembly 200 can be used. In other examples, a disinfection system can be used. The example sterilizing system 100 can include, for example, sterilization chamber 110 with door 111, seal 112, atomizer inlet 113, vent 114, air filter 115, temperature sensor 116, and relative humidity sensor 117; vacuum hookup connection 120 with gas flow meters 122, vacuum control valve 123, chamber vacuum control valve 124, vacuum pumps 127, filters 125, 126, 128, and muffler 129; atomizer assembly 130 with sterilant 131, chemical inlet 132, chemical pump 133, chemical flow meters 134, air inlet 135, pressure regulator 136, air filter 137, air flow control 138, air valve 139, atomizer purge 140, and pressure transducers 141; in addition to controller 150 with user interface 155 and sampling assembly 200.

The sterilization chamber 110 can include, for example, a chamber for insertion of medical equipment or other items to be sterilized. The sterilization chamber 110 can be of any appropriate size for the items to be sterilized. For example, in some examples, the sterilization chamber 110 can be about 300 to about 500 L. In some examples, the sterilization chamber 110 can be about 2,000 to about 4,000 L. The sterilization chamber 110 can be accessed by a user by, for example, the door 111. The door 111 can be, for example, on one side of the sterilization chamber 110, and the door 111 can be large enough to allow for insertion of the items for sterilization. The door 111 can be, for example, airtight so that a vacuum can be applied inside the sterilization chamber 110 for sterilization of the medical equipment or other items. In some examples, the door 111 can be shut with a seal 112 in or around the door 111. In some cases, such as with a disinfection system, a disinfection environment can be used instead of a sterilization chamber.

The sterilization chamber 110 can have, in or on one or more sides, an atomizer inlet 113 and a vent 114. The atomizer inlet 113 can allow for influx of a chemical composition, such as one or more sterilant or disinfectant, into the sterilization chamber 110 to interact with and sterilize or disinfect the medical equipment or other items. The sterilant or disinfectant can be, for example, atomized, vaporized, or in other gaseous form, as desired, for sterilization.

The vent 114 in the sterilization chamber 110 can allow for venting of the sterilization chamber as desired. Venting of the environment inside the sterilization chamber can be performed, for example, to maintain a particular pressure inside the chamber, or to alter the pressure inside the chamber over time. An air filter 115, such as a HEPA air filter, can, for example, be in fluid communication with the vent 114, to allow gas or air to pass out of the sterilization chamber 110 and be filtered for chemicals, as the gas leaves the sterilization chamber 110.

The sterilization chamber 110 can also include, for example, a number of sensors, such as a temperature sensor 116, a relative humidity sensor 117, combinations thereof, or other sensors such as pressure, optical, flow rate sensors, or combinations thereof. The sensors 116, 117, or other additional sensors, can, for example, be in communication with a controller or processor, such as controller 150, to allow manipulation of the sterilization process in the sterilization chamber 110 based on parameters sensed, such as temperature or humidity.

The vacuum hookup connection 120 can connect the sterilization chamber 110 to a vacuum source. The vacuum hookup connection 120 can include, for example, the gas flow meters 122, the vacuum control valve 123, the chamber vacuum control valve 124, the vacuum filters 125, 126, 128 the vacuum pumps 127, and the muffler 129.

The vacuum hookup connection 120 can allow for an airtight connection between the sterilization chamber 110 and the vacuum system. The vacuum system can, for example, include one or more gas flow meters 122 to monitor the flow of gas in and out of the sterilization chamber 110 before, during, and after a sterilization cycle.

The valves 123, 124, can allow for specific control of the flow rate of gas in the vacuum system, so as to create a specific pressure inside the sterilization chamber 110. The vacuum filters 125, 126, 128, also along the vacuum lines, can allow for cleaning of air being used in the vacuum system. The filters can include, for example, polypropylene filters, sodium bicarbonate filters, potassium permanganate filters, and other types of filters appropriate for a vacuum sterilization system.

The vacuum pumps 127 can, for example, create a vacuum along the vacuum system so as to induce a vacuum in the sterilization chamber 110. The muffler 129 can, for example, minimize noise created by the vacuum system.

The atomizer assembly 130 can include, for example, a sterilant 131, a chemical inlet 132, a chemical pump 133, chemical flow meters 134, an air inlet 135, a pressure regulator 136, an air filter 137, an air flow control 138, an air valve 139, an atomizer purge 140, and one or more pressure transducers 141.

In system 100, a sterilant is atomized for the sterilization process inside the sterilization chamber 110. In some sterilization systems, a sterilant is vaporized, or supplied as a liquid. In some sterilization systems, the sterilant is atomized or vaporized in a separate chamber, and then pumped or run into the sterilization chamber. The sampling assembly 200 can be used, for example, in any of these types of sterilization systems.

In the example sterilization system 100 shown in FIG. 1, the sterilant 131 is stored as fluid in bottles. In some examples, other containers, with various shapes or storage methods, could be used.

The sterilant 131 is connected to the chemical inlet 132 into the atomizer assembly 130, and the sterilant can be moved, for example, by the chemical pump 133, and the rate of movement of the sterilant can be monitored by the chemical flow meters 134.

At the air inlet 135 of the atomizer assembly 130, air (or other gas) can enter the atomizer assembly 130 for use in atomizing the sterilant. The pressure regulators 136 can monitor the pressure of the air in the atomizer assembly 130 to allow proper atomization of the sterilant. One or more air filters 137, air flow controls 138, and air valves 139, can be used in manipulating the flow of air and sterilant to induce atomization of the sterilant in the sterilization chamber 110. The atomizer purge 140 can allow for venting or dumping of excess air or sterilant depending on pressure feedback. The pressure transducers 141 can, for example, monitor the pressure of sterilant as it is atomized.

In system 100, the controller 150 can be in communication with the vacuum system, atomizer assembly 130, and the sterilization chamber 110. The controller 150 can, for example, include a processor and memory that can received sensed data from the various sensors in the system, and direct changes in the valves or air lines within the system. The controller 150 can, for example, manipulate the pressure in the sterilization chamber created by the vacuum system, and the amount and rate of atomized sterilant entering the system.

The controller 150 can be, for example, connected to a user interface 155, so as to communicate this information to the user. The user interface can, for example, include a screen, or one or more user-actuated buttons or triggers to allow to user to read information and alter the sterilization process as desired.

Sampling assembly 200 can be used inside the sterilization chamber 110 of the system 100 to verify the sterilization processes of the system 100. The sampling assembly 200 can be placed or located physically inside the sterilization chamber 110, either loose or mounted to the inside of the sterilization chamber 110. The sampling assembly 200 can carry in it one or more indicators, such as biological indicators or chemical indicators, that can react with the atomized sterilant when a sterilization cycle is run on the system 100. The sampling assembly 200 is discussed in more detail with references to FIGS. 2A-2C and 3A-3B below.

The sterilization system 100 discussed herein is one example of a sterilizing or disinfecting system in which a sampling assembly, such as the sampling assembly 200, can be used. In some examples, a different types of disinfection or sterilization system can be used.

Figure 2A:
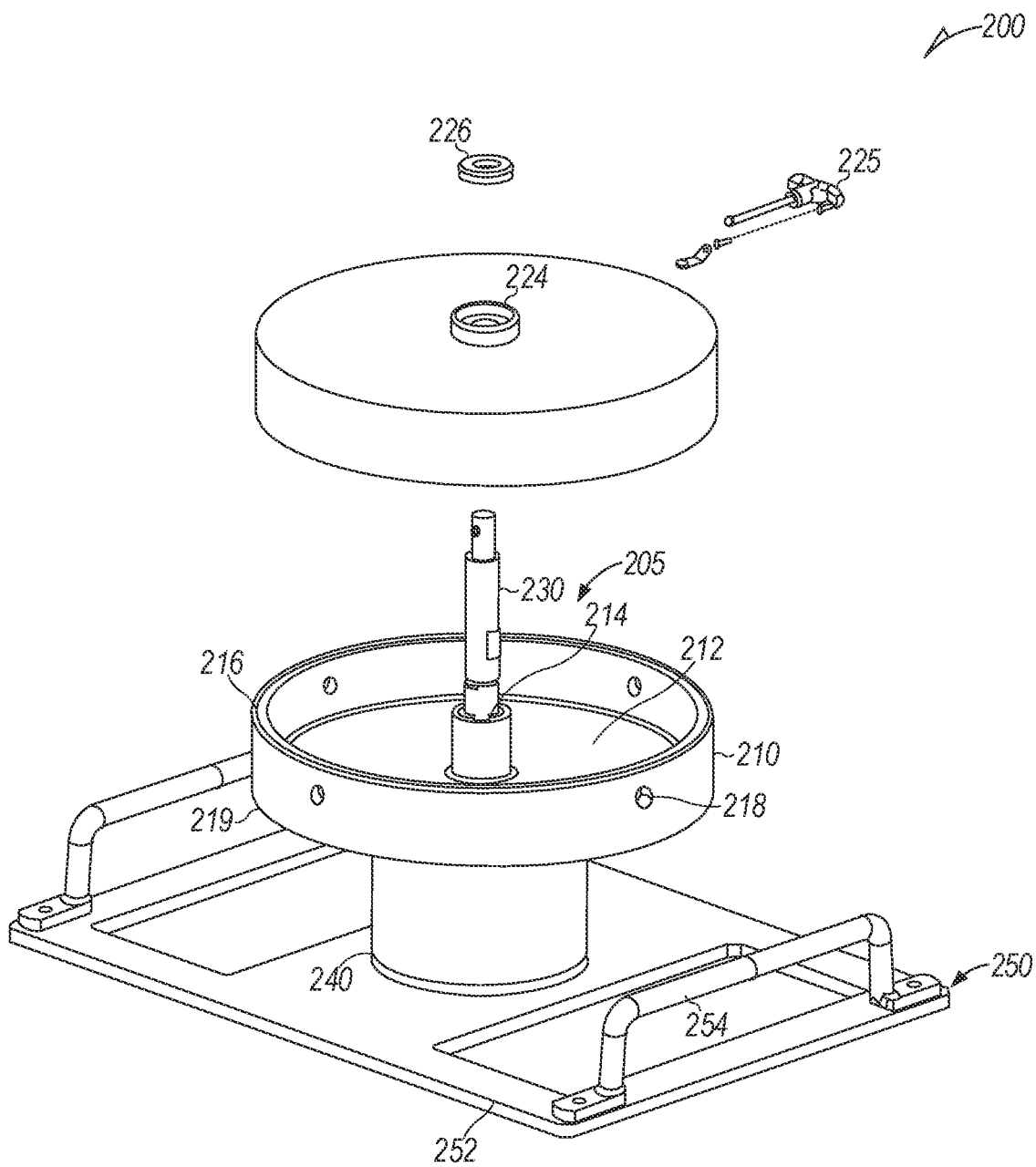
FIG. 2A is an exploded view of a sampling assembly for verifying the environment in a sterilizing or disinfecting system.
Figure 2C:
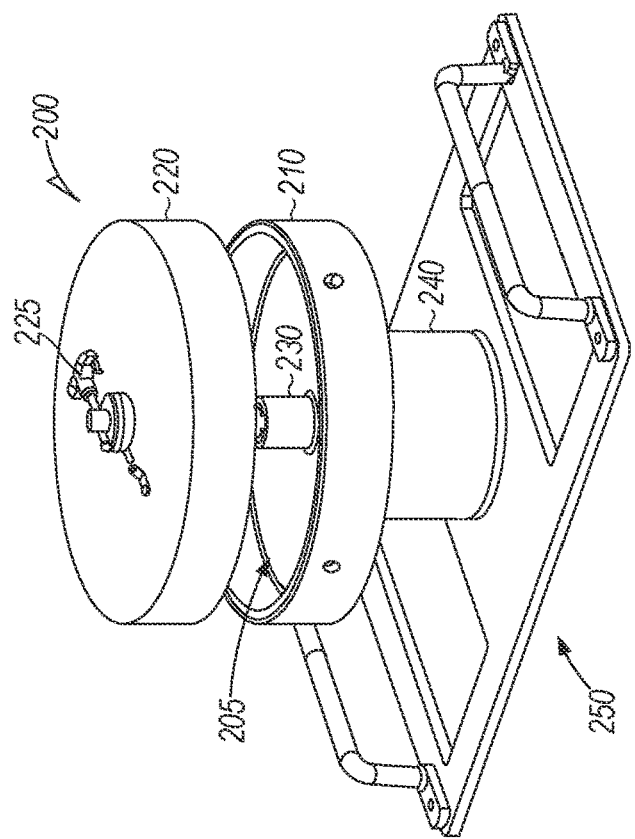
FIGS. 2B-2C are perspective views of the sampling assembly from FIG. 2A, for verifying the environment in a sterilizing or disinfecting system.
Figure 2B:
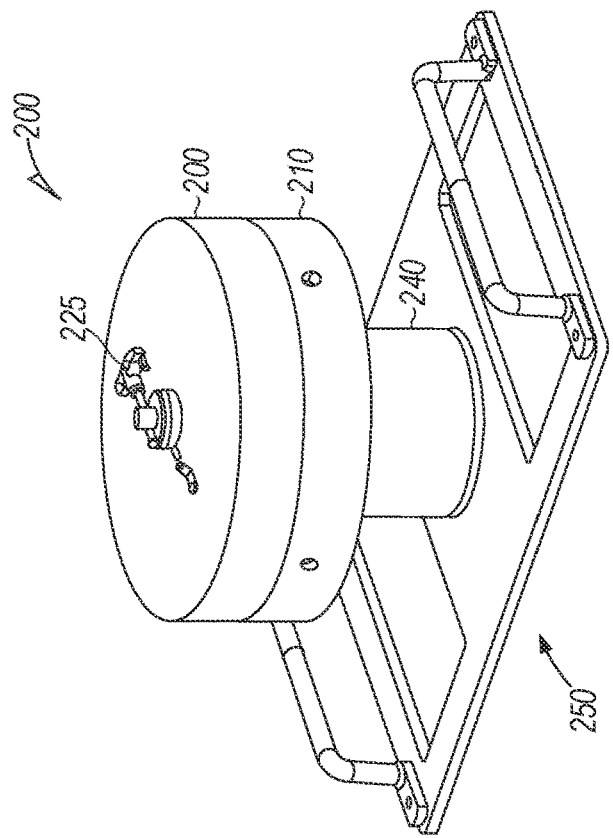

FIG. 2A is an exploded view of a sampling assembly 200 for verifying the environment in a sterilizing or disinfecting system. FIGS. 2B-2C are perspective views of the sampling assembly 200, for verifying the environment in a sterilizing or disinfecting system. FIG. 2B depicts the sampling assembly 200 in a closed position, while FIG. 2C depicts the sampling assembly 200 in an open position. FIGS. 2A-2C will be discussed together.

Assembly 200 can include, for example, chamber 205 with bottom portion 210 and top portion 220. Bottom portion 210 can include, for example, tray 212, central opening 214, sealing groove 216, and fluid flow ports 218, 219; top portion 220 with central opening 224, locking pin 225, and sealing ring 226; central pin 230; actuator 240; and base 250 with platform 252 and handles 254.

Chamber 205 can be, for example, for holding indicators, such as biological or chemical indicators, for validating sterilization in a sterilization system. In some cases, chamber 205 can be adapted for capturing a portion of the atmosphere inside a sterilization system, so that the atmosphere can be tested. Chamber 205 can include, for example, a bottom portion 210 and a top portion 220 such that the chamber 205 can open or close when inside a sterilization system for testing or validation of the sterilization process while the sterilization process is running.

The bottom portion 210 can include, for example, a tray 212 for holding biological or chemical indicators. The tray 212 can be shaped to hold in place one or more indicators during a sterilization or disinfection process. In some cases, the bottom portion 210 can further include a rack configured for holding indicators.

The bottom portion 210 can additionally include one or more fluid flow ports 218, 219. The fluid flow ports 218, 219 can be adapted for venting the sampling assembly 200. In some cases, one or more of the fluid flow ports can be adapted for creating a vacuum in the sampling assembly 200.

The top portion 220 can act as a lid for the bottom portion 210, together creating a chamber 205 for sampling a sterilization or disinfection atmosphere. The top portion 220 and the bottom portion 210 can, for example, have the same diameter to allow sealing together into one chamber 205.

The locking pin 225 can be located in the top portion 220 to allow for locking of the chamber 205 when open, and prevents accidental closing of the top portion 220 onto the bottom portion 210. The locking pin 225 can be, for example, a safety pin. The locking pin 225 can be, for example, a quick release pin to better access the load of the sampling assembly 200.

The central pin 230 can run between the top portion 220 and the bottom portion 210, allowing the portions to stack on top of one another and seal to each other at the sealing groove 216. In some examples, the central pin 230 can have one or more ridges to prevent the top portion 220 or the bottom portion 210 from unintentionally moving towards the other portion. For example, the central pin 230 can have an upper ridge for preventing the top portion 220 from collapsing onto the bottom portion 210, except when desired. For example, the central pin 230 can have a lower ridge for preventing the bottom portion 210 from moving upwards towards the top portion 220, except when desired.

The central opening 214 in the bottom portion 210 and the central opening 224 in the top portion 220 can be aligned to each other, and can be fitted to the central pin 230. One or more sealing rings 226 can be used to seal the central pin 230 to the chamber 205 when in use, to allow an airtight chamber 205. The sealing rings 226 can be, for example, silicone, or other material, such as in an O-ring shape. The sealing rings 226 can be, for example, attached to the opening 224 with an adhesive. The sealing rings 226 can, for example, level the central pin 230 within the assembly 200. The central openings 214, 224, can have, for example, the sample diameter for fitting the central pin 230.

The actuator 240 can be, for example, an actuator located below the bottom portion 210. The actuator 240 can be, for example, for lifting up and separating the top portion 220 from the bottom portion 210. In some examples, the actuator 240 can actuate the central pin 230 to induce opening of the chamber 205.

The actuator 240 can be, for example, a pneumatic actuator, an electrical actuator, a mechanical actuator, a hydraulic actuator, a combination thereof, or another type of actuator. The actuator can be initiated, for example, by an external controller in communication with the sampling assembly 200 while the sterilization or disinfection cycle is running. The actuator 240 can, for example, be programmed to open for a specific period of time, such as during a particular portion of the sterilization or disinfection cycle. This is discussed in more detail with reference to FIG. 4 below.

The base 250 can include a mounting platform 252 and handles 254. The base 250 can serve as a bottom for the assembly 200. The actuator 240 can be, for example, mounted to platform 252 so that the assembly 200 is secured. The handles 254 can allow for easy movement of the sampling assembly 200 into or out of a sterilization or disinfection system.

The assembly 200 can be, for example, inserted into the chamber of a sterilization or disinfection system for verification of that sterilization or disinfection system. In some cases, the assembly 200 can be inserted into the chamber of the system to test the atmosphere in that chamber. When inserted, the assembly 200 can be, for example, in a closed position (e.g., a first position) such as shown in FIG. 2B. In the closed position, the assembly 200 can be airtight to prevent entrance of the atmosphere in the sterilization or disinfection chamber or environment into to the assembly 200 until the desired portion of the sterilization or disinfection cycle.

When verification is desired, the actuator 240 can be initiated to open the assembly 200, separating the top portion 220 from the bottom portion 210. While in an open position (e.g., a second position), such as shown in FIG. 2C, the sampling assembly 200 chamber 205 can collect a sample of the atmosphere in the sterilization or disinfection system, such as a mixture of air and atomized or vaporized sterilant or disinfectant. In some cases, the sampling assembly 200 can capture a portion of the atmosphere. In some cases, the sampling assembly can host one or more indicators that can react with the atmosphere.

When the desired exposure time is finished, the actuator 240 can be initiated to close the sampling assembly 200 back to the closed position of FIG. 2B. When the sterilization or disinfection cycle is complete, the user can remove the sampling assembly 200 from the sterilization or disinfection system and test the sample to verify the sterilization process. In some cases, the sampling assembly 200 can be left in the sterilization or disinfection system after the sterilization or disinfection cycle, and the sample can be removed for testing and verification, without removing the entire sampling assembly 200.

Figure 3B:
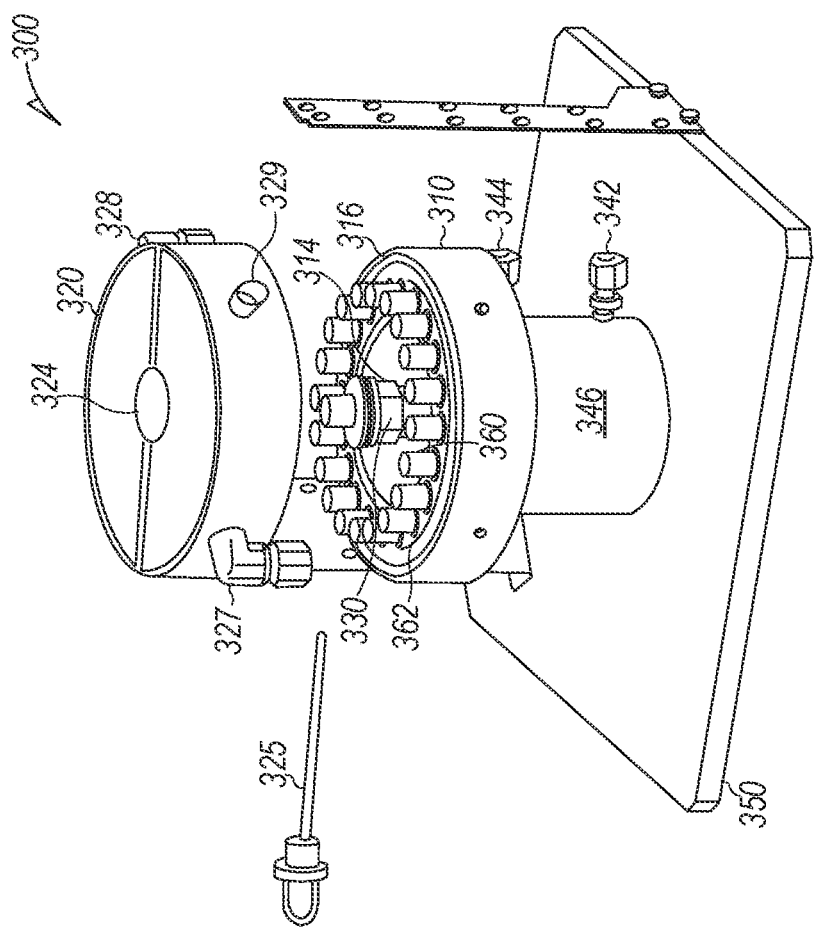
FIGS. 3A-3B are perspective views of the sampling assembly, for verifying the environment in a sterilizing or disinfecting system, in an additional example.
Figure 3A:
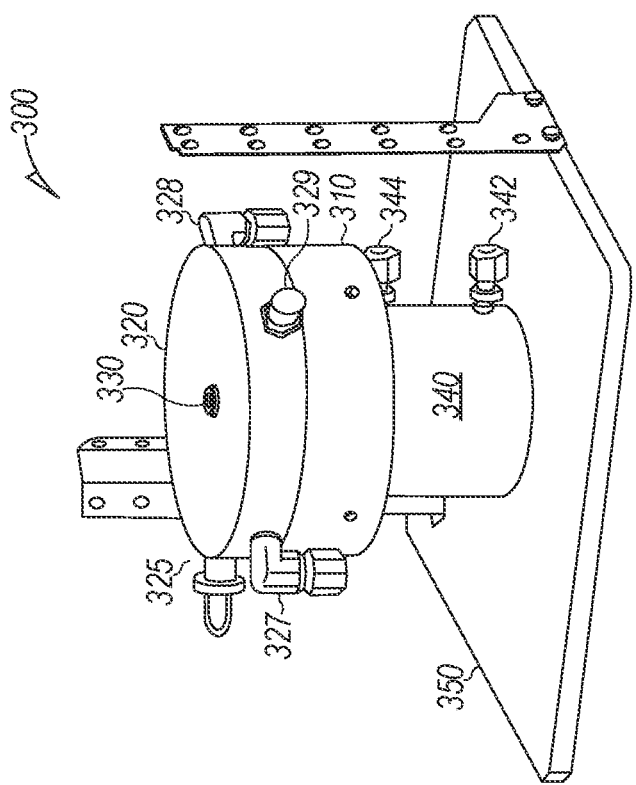

FIGS. 3A-3B are perspective views of a sampling assembly 300, for verifying the environment in a sterilizing or disinfecting system, in an additional example. The components of sampling assembly 300 are similar to the corresponding components of sampling assembly 200, except where otherwise noted.

Assembly 300 can include, for example, bottom portion 310 with tray 312, central opening 314, sealing grove 316; top portion 320 with central opening 324, locking pin 325, and fluid flow ports 327, 328, 329; central pin 330; actuator 340 with ports 342, 344; and base 350. Assembly 300 can additionally include indicators 360 in holder 362.

In sampling assembly 300, fluid flow ports 327, 328, 329 are located on the top portion 320. The fluid flow ports 327, 328, 329, can be, for example, vent ports, evacuation or purge ports, or vacuum ports. In some examples, one or more of the ports can be plugged if they are not desired for that particular sampling session.

For example, if one or more of the ports is adapted for creation of a vacuum in the sampling assembly 300, a vacuum can be induced in the sampling assembly 300 before or at the beginning of the sterilization or disinfection cycle as desired. The chamber 305 can then be vented as needed to maintain a vacuum.

In some examples, the one or more ports can be an evacuation or purge port, such that when the sampling assembly 300 is inserted into the sterilization or disinfection chamber, and the chamber is prepared for sterilization or disinfection, the inside of the chamber 305 of the sampling assembly 300 can be purged of other residual gas or air prior to the sterilization process. In some cases, the ports can be used to clean out the sampling assembly 300.

In sampling assembly 300, the actuator 340 has two ports 342, 344. The ports 242, 244, can be, for example, adapted for initiating pneumatic action of the actuator 340. This can be performed, for example, by inserting fluid through one or more of the ports 342, 344, and as needed draining the fluid back out, so that the pneumatic actuator 340 can move to the appropriate heights for opening or closing the sampling assembly 300.

In sampling assembly 300, several indicators 360 reside in the holder 362 residing in the bottom portion 310 of the chamber 305. The indicators 360 can be, for example, biological indicators or chemical indicators.

Biological indicators can, for example, be affected by microorganisms left in the sterilization chamber. In general, biological indicators can be measured for a D-value indicating how long it takes to reduce a microorganism population by 90%, or the time needed to 1-log reduction of microorganisms. Where multiple biological indicators are used together in the sampling assembly 300, all the biological indicators can be affected by the atmosphere in the sterilization or disinfection chamber simultaneously. For example, five, ten, twenty, or more biological indicators can be used simultaneously to allow for statistical analysis of multiple biological indicators. Biological indicators can be analyzed, for example, with ISO Standard Procedures 14937, 11135, or similar.

Chemical indicators can indicate whether an amount of a particular chemical, such as a component of a sterilant, is present, and if it is present in a threshold concentration. In some cases, chemical indicators can indicate a property of chemicals in the sterilization or disinfection chamber, such as pH. Multiple chemical indicators can be used simultaneously in the sampling assembly 300, so as to allow statistical analysis.

The indicators can reside, for example, in the holder 362. The holder 362 can be cut specifically to fit snugly in the bottom portion 310. The holder 362 can be removeable from the bottom portion 310, or can be attached to the bottom portion 310, such as by bolts, adhesive, or other attachment mechanisms. The holder 362 can have generic holds, bars, or shelves to hold indicators. In some cases, the holder 362 can be cut specifically to hold a particular type and size of indicator. Where multiple holes are cut into the holder 362 for holding indicators, the holes can be evenly spaced to allow even exposure of indicators within the sampling assembly 300.

In some cases, indicators are not used. Instead, the chamber 305 can be used to capture a portion of the atmosphere, such as the gas and sterilant or disinfectant mixture, inside the chamber of the sterilization or disinfection system. The sampling assembly 300 can, for example, capture less than 10% or less than 5% volume of the sterilization or disinfection chamber. In this case, the chamber 305 could be resealed around the gaseous sample, and after the sterilization cycle has concluded, the sampling assembly 300 could be removed and the gaseous sample tested.

For larger sterilization or disinfection chambers or environments, more than one sampling assembly could be used in the same sterilization or disinfection chamber, such as, at various portions of the floor of the sterilization or disinfection chamber, evenly spaced or not evenly spaced. In some cases, the sampling assemblies could be mounted to one or more walls of the sterilization or disinfection chamber.

Figure 4:
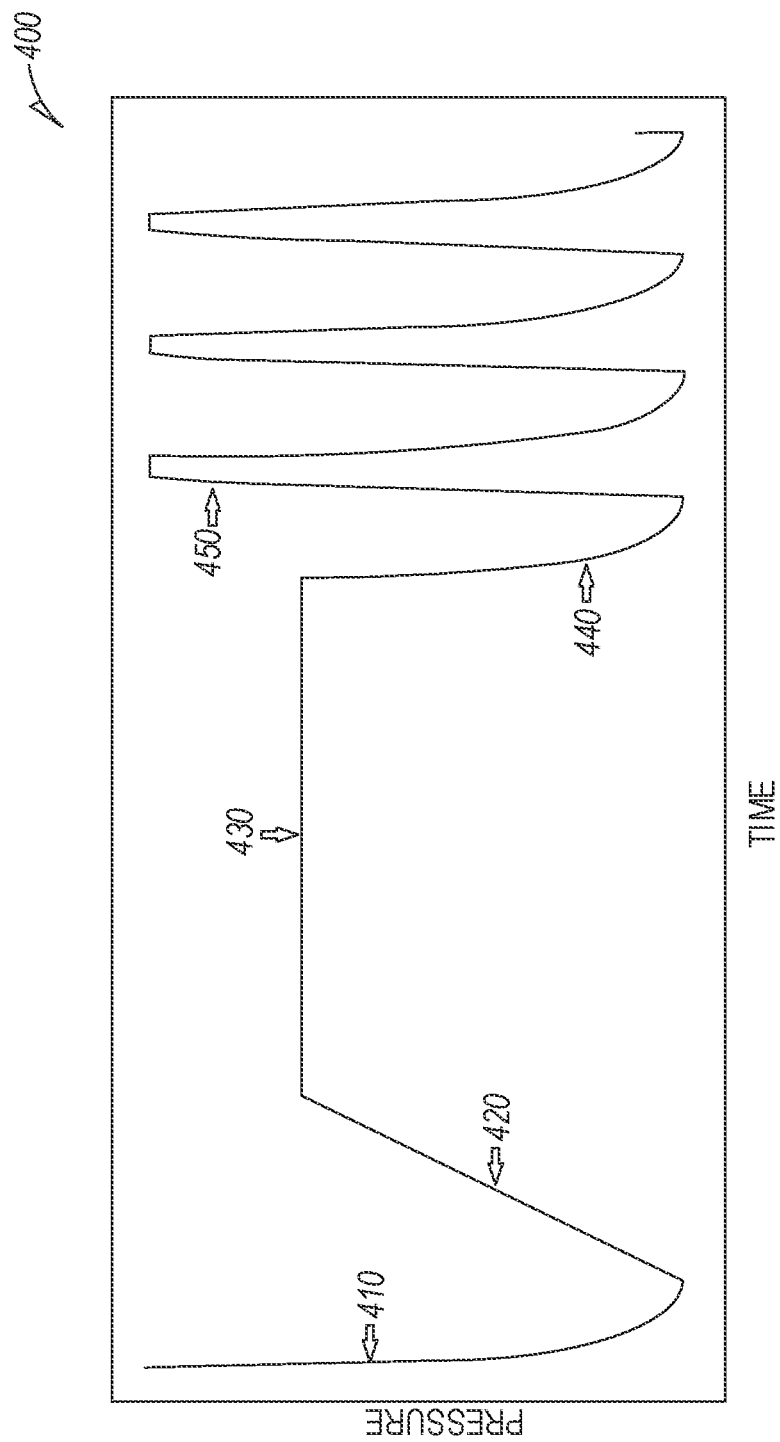
FIG. 4 is a graphical illustration of a cycle in a sterilizing or disinfecting system.

FIG. 4 is a graphical illustration of an example cycle 400 in a sterilizing or disinfecting system. The cycle 400 includes an evacuation phase 410, an injection phase 420, a hold time 430, a post-injection evacuation phase 440, and a ventilation phase 450.

In the evacuation phase 410, the sampling assembly can be located in the sterilization or disinfection chamber, and the sterilization or disinfection chamber can optionally be sealed. Subsequently, the sterilization or disinfection chamber can optionally be vacuumed (e.g., evacuated) to create the desired pressure inside the sterilization or disinfection chamber.

In the injection phase 420, one or more sterilants and/or disinfectants can be injected into the sterilization or disinfection chamber. In some cases, the sterilant or disinfectant can be atomized or vaporized. In some cases, the sterilant or disinfectant can be directly injected into the chamber, or can be pumped from a separate channel.

In the hold time 430, the pressure and amount of sterilant or disinfectant can be held steady to allow for sterilization or disinfection. During the hold time 430, the sampling assembly can be, for example, opened to expose indicators to the atmosphere in the chamber. The sampling assembly can be again closed by the end of the hold time 430. In other cases, the sampling assembly can be opened during different phases of the sterilization or disinfection cycle.

In the post-injection evacuation phase 440, the chamber can again be vented or evacuated to manipulate the pressure in the chamber. In the ventilation phase 450, the chamber can be vented.

Figure 5:
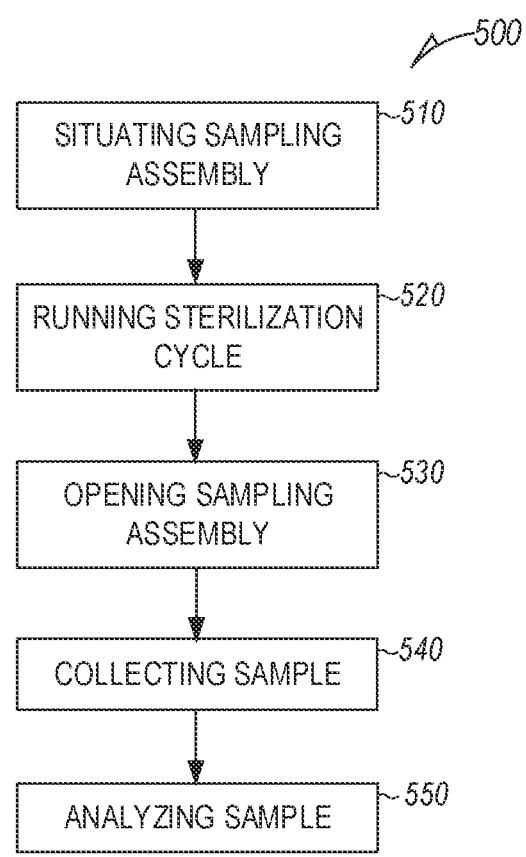
FIG. 5 is a flowchart depicting a method of using a sampling assembly for verifying the environment in a sterilizing or disinfecting system.

FIG. 5 is a block diagram depicting a method 500 of using a sampling assembly for verifying the environment in a sterilizing or disinfecting system. In method 500, a user can situate a sampling assembly in a sterilizing or disinfecting system, run the sterilization or disinfection cycle, open the sampling assembly during a portion of the sterilization or disinfection cycle, and collect a sample in the sampling assembly, followed by analysis of that sample.

The sampling assembly can be, for example, the assembly 200 or 300 discussed above. The sampling assembly can be set inside the sterilization or disinfection chamber (operation 510), or attached to the chamber, such as by bolts, adhesive, or other attachment mechanisms. In some cases, more than one sampling assembly can be used in the sample cycle. The sampling assembly can be, for example, closed and sealed so that it is airtight prior to the sterilization cycle.

In operation 520, the sterilization or disinfection cycle can be run. The cycle can, for example, include an evacuation phase wherein the chamber is vacuumed, an injection phase where a sterilant and/or disinfectant is injected into the chamber, a hold phase where the pressure is held, a post-injection evacuation phase where the chamber is vacuumed, and a validation phase.

The sampling assembly can be opened during the sterilization or disinfection cycle (operation 530). The sampling assembly can be closed later in the sterilization or disinfection cycle, such that a sample is collected while the sampling assembly is open and exposed to the atmosphere of the sterilization or disinfection chamber (operation 540). In some cases, the sampling assembly can be opened at the beginning of the hold phase and closed at the end of the hold phase. In some cases, the sampling assembly can be opened at closed during one or more of the cycle phases.

The sampling assembly can include, for example, one or more biological indicators, one or more chemical indicators, or can be used to capture a portion of the atmosphere inside the sterilization or disinfection chamber. The sample can then be analyzed to validate the sterilization or disinfection cycle (operation 550).

Various Notes & Examples

Each of these non-limiting examples can stand on its own, or can be combined in various permutations or combinations with one or more of the other examples.

Example 1 can include a device for use in a disinfection process, the device comprising: a sampling assembly capable of a first position and a second position, wherein the sampling assembly is configured to be used inside a disinfection system, the sampling assembly comprising: a top portion; a bottom portion; at least one seal therebetween such that the top portion and the bottom portion form an airtight compartment when in the first position; a central pin running through the top portion and bottom portion; and an actuator configured to move the sampling assembly between the first position and the second position along the central pin during a portion of the sterilization process, such that the sampling assembly can collect a sample of atmosphere within the sterilization system.

Example 2 can include Example 1, further comprising a base, wherein the sampling assembly is mounted to the base.

Example 3 can include any of Examples 1-2, further comprising a quick release pin in the top portion of the sampling assembly, the quick release pin configured to prevent movement between the first position and the second position.

Example 4 can include any of Examples 1-3, wherein the actuator comprises a pneumatic actuator, a hydraulic actuator, an electrical actuator, or a mechanical actuator.

Example 5 can include any of Examples 1-4, wherein the sampling assembly further comprises a first fluid flow port for venting the airtight compartment of the sampling assembly.

Example 6 can include any of Examples 1-5, wherein the sampling assembly further comprises a second fluid flow port for evacuating the airtight compartment of the sampling assembly.

Example 7 can include any of Examples 1-6, wherein the at least one seal comprises a first seal between the bottom portion and the top portion, the first seal being around an outer diameter of the bottom portion.

Example 8 can include any of Examples 1-7, wherein the top portion and the bottom portion each comprise a central hole through which the central pin extends.

Example 9 can include any of Examples 1-8, further comprising a second seal between the bottom portion and the top portion, the second seal around a diameter of the central hole around the central pin.

Example 10 can include any of Examples 1-9, wherein the central pin comprises a first ridge configured to hold the top portion up when moving the sampling assembly from the first position to the second position.

Example 11 can include any of Examples 1-10, further comprising a section for holding a specimen or other item under study within the airtight compartment.

Example 12 can include any of Examples 1-11, further comprising a rack for holding chemical or biological indicators in the bottom portion.

Example 13 can include any of Examples 1-12, further comprising the disinfection system, wherein the sampling assembly resides in a chamber of the disinfection system.

Example 14 can include a method of validating a disinfecting system, comprising: situating a sampling assembly in a chamber of the disinfecting system, the sampling assembly comprising: a top portion; a bottom portion; and at least one seal therebetween such that the top portion and the bottom portion form an airtight compartment; running a disinfection cycle on the disinfecting system; opening the sampling assembly during a portion of the disinfection cycle; collecting a sample in the sampling assembly; and analyzing the sample.

Example 15 can include Example 14, wherein the disinfection cycle comprises: an evacuation phase where the chamber is conditioned; an injection phase where a disinfectant is injected into the chamber; a hold phase where the pressure in the chamber is held; a post-injection evacuation phase where the chamber is vacuumed; and a validation phase.

Example 16 can include any of Examples 14-15, wherein opening the sampling assembly is performed during the hold phase.

Example 17 can include any of Examples 14-16, further comprising closing the sampling assembly during the hold phase.

Example 18 can include any of Examples 14-17, wherein collecting a sample comprises exposing one or more biological indicators situated in the sampling assembly to the chamber.

Example 19 can include any of Examples 14-18, wherein collecting a sample comprises exposing one or more chemical indicators situated in the sampling assembly to the chamber.

Example 20 can include any of Examples 14-19, wherein collecting a sample comprises taking in a portion of atmosphere of the chamber into the sampling assembly.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device (including processing circuitry within such electronic device) to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The following claims are hereby incorporated into the Detailed Description as examples or embodiments, with each claim standing on its own as a separate embodiment, and it is contemplated that such embodiments can be combined with each other in various combinations or permutations.

What is claimed is:

1. A device for use in a disinfection process, the device comprising:
 a sampling assembly capable of a first position and a second position, wherein the sampling assembly is configured to be used inside a disinfection system, the sampling assembly comprising:
 a top portion;
 a bottom portion;

at least one seal therebetween such that the top portion and the bottom portion form an airtight compartment when in the first position;

a central pin running through the top portion and bottom portion; and an actuator configured to move the sampling assembly between the first position and the second position along the central pin during a portion of the disinfection process, such that the sampling assembly can collect a sample of atmosphere within the disinfection system.

2. The device of claim 1, further comprising a base, wherein the sampling assembly is mounted to the base.

3. The device of claim 1, further comprising a quick release pin in the top portion of the sampling assembly, the quick release pin configured to prevent movement between the first position and the second position.

4. The device of claim 1, wherein the actuator comprises a pneumatic actuator, a hydraulic actuator, an electrical actuator, or a mechanical actuator.

5. The device of claim 1, wherein the sampling assembly further comprises a first fluid flow port for venting the airtight compartment of the sampling assembly.

6. The device of claim 5, wherein the sampling assembly further comprises a second fluid flow port for evacuating the airtight compartment of the sampling assembly.

7. The device of claim 1, wherein the at least one seal comprises a first seal between the bottom portion and the top portion, the first seal being around an outer diameter of the bottom portion.

8. The device of claim 1, wherein the top portion and the bottom portion each comprise a central hole through which the central pin extends.

9. The device of claim 8, further comprising a second seal between the bottom portion and the top portion, the second seal around a diameter of the central hole around the central pin.

10. The device of claim 1, wherein the central pin comprises a first ridge configured to hold the top portion up when moving the sampling assembly from the first position to the second position.

11. The device of claim 1, further comprising a section for holding a specimen or other item under study within the airtight compartment.

12. The device of claim 1, further comprising a rack for holding chemical or biological indicators in the bottom portion.

13. The device of claim 1, further comprising the disinfection system, wherein the sampling assembly resides in a chamber of the disinfection system.

* * * * *